United States Patent [19]

Monchalin et al.

[11] Patent Number: 5,080,491

[45] Date of Patent: Jan. 14, 1992

[54] LASER OPTICAL ULTARASOUND DETECTION USING TWO INTERFEROMETER SYSTEMS

[75] Inventors: Jean-Pierre Monchalin, Montreal; René Heon, McMasterville, both of Canada

[73] Assignee: National Research Council Canada, Ottawa, Canada

[21] Appl. No.: 606,820

[22] Filed: Oct. 31, 1990

[30] Foreign Application Priority Data

Jan. 4, 1990 [CA] Canada .................................. 2007190

[51] Int. Cl.⁵ ........................................................ G01B 9/02
[52] U.S. Cl. ........................................ 356/352; 356/358; 73/657
[58] Field of Search ................... 356/352, 358; 73/655, 73/657

[56] References Cited

U.S. PATENT DOCUMENTS

| | | | |
|---|---|---|---|
| 4,345,475 | 8/1982 | Bickel | 73/655 |
| 4,360,272 | 11/1982 | Schmadel et al. | 356/352 |
| 4,379,633 | 4/1983 | Bickel et al. | 73/657 |
| 4,659,224 | 4/1987 | Monchalin | 356/352 |
| 4,966,459 | 10/1990 | Monchalin | 356/352 |

OTHER PUBLICATIONS

Monchalin, J. P., IEEE Transactions on Ultrasonics, Ferroelectrics and Frequency Control, vol. UFFC-33, No. 5, Sep. 1986, pp. 485-489.
Stokes, L. F. et al., Optics Letters, vol. 7, No. 6, Jun. 1982, pp. 288-290.

*Primary Examiner*—Samuel Turner
*Attorney, Agent, or Firm*—Foley & Lardner

[57] ABSTRACT

A laser ultrasound detection technique which is insensitive to laser intensity fluctuations, perturbation at the object surface and the like is disclosed. The invention consists of two substantially identical interferometers of the Fabry-Perot type or such an interferometer with a birefringent element in its optical cavity. The interferometers have resonance frequencies higher and lower than the laser frequency so that noises can be cancelled out by signal processing.

17 Claims, 3 Drawing Sheets

LASER OPTICAL ULTRASOUND DETECTION USING TWO INTERFEROMETER SYSTEMS

FIELD OF THE INVENTION

The present invention relates generally to detection of ultrasound by laser beam and in particular, it is directed to non-contact detection of ultrasound travelling in or at the surface of an object by means of laser beam which undergoes phase modulation when it is scattered from the surface of the object.

BACKGROUND OF THE INVENTION

Ultrasonic inspection is one of the most important nondestructive techniques for inspecting materials and structures. Conventional ultrasonic inspection suffers from two important limitations: first, there is need of contact between the transducer and the inspected part or need of coupling fluid bath or fluid column (such as water) to transmit ultrasound and secondly the transducer should be properly oriented with respect to the surface when single side inspection is performed (operation in reflection or pulse echo mode). Thus, inspection of samples at elevated temperature or complex geometry is difficult. These limitations are circumvented by laser-ultrasonics, an ultrasonic inspection technique which uses lasers to generate and detect ultrasound. For generation, a high power short pulse laser is generally used and the ultrasonic waves are produced by the surface stresses induced by the heat source deposited by laser absorption or by the recoil effect following surface ablation. For detection, a continuous wave or long pulse laser is used in association with an interferometer which demodulates the frequency shift produced by the ultrasonic surface motion and gives a signal representative of this motion.

For industrial inspection, in contrast to investigations in a laboratory, interferometers based on velocity interferometry are preferred, as explained in a review paper "Optical Detection of Ultrasound" by J-P Monchalin published in the IEEE Transactions on Ultrasonics, Ferroelectrics and Frequency Control, September 1986, pp. 485–499. In U.S. Pat. No. 4,659,224 Apr. 21, 1987, the present inventor teaches how a confocal Fabry-Perot interferometer can be advantageously used as interferometric receiver for ultrasound. Such a system permits to receive many optical speckles from a large spot on the surface of the sample and its detection bandwidth can be optimized by proper choice of mirror reflectivities. In this system the laser frequency is tuned to the slope of the Fabry-Perot transmission peak.

In his copending patent application U.S. Ser. No. 07/310,380 filed on Feb. 15, 1989 now U.S. Pat. No. 4,966,459, now the present inventor describes how a confocal Fabry-Perot interferometer can be used in a different way to provide broadband detection capability. The confocal Fabry-Perot is used in this case to strip the incoming light from the sample from its optical sidebands produced by the ultrasonic surface motion or transient motion. This scheme consists in using a Fabry-Perot in the reflection mode and not in the transmission mode as described in the above U.S. patent. The interference effect occurs at the front mirror, between the light directly reflected by this mirror and light stripped from its sidebands reflected by the optical confocal cavity.

For both of these detection schemes which use a confocal Fabry-Perot (or a multiple-wave interferometer of the confocal Fabry-Perot type), the detectivity and the signal-to-noise ratio improve for higher laser power when the noise in the signal is caused by the fundamental quantum nature of light (quantum noise or photon noise or shot noise). In this case, the noise and the signal-to-noise ratio vary as the square root of the power received by the detector. In practice, lasers have fluctuating intensities, so when the power received by the detector is increased, either because the surface has a better reflectivity or by increasing the laser power (such as sending it through an optical amplifier), a level is reached where the noise essentially originates from the laser intensity fluctuations. When this level is reached it becomes useless to increase further the received power, since the signal-to-noise ratio (and consequently the minimum detectable ultrasonic or transient surface motion) becomes independent of the received power. This limitation also occurs when the light reflected by the surface through the collecting aperture of the system is constantly varying, such as in the case of a liquid agitated by waves and ripples at its surface. The present invention overcomes these difficulties.

OBJECTS OF THE INVENTION

It is therefore an object of the present invention to provide a non-contact non-destructive ultrasonic inspection method and apparatus.

It is another object of the present invention to provide a ultrasonic inspection method and apparatus which are not sensitive to laser intensity variation.

It is further object of the present invention to provide a ultrasonic inspection method and apparatus which are not sensitive to disturbances at the surface of an object.

It is still an object of the present invention to provide a ultrasonic inspection apparatus which includes two substantially identical Fabry-Perot interferometers or a Fabry-Perot interferometer having different resonance peaks for different polarizations of a laser beam.

SUMMARY OF THE INVENTION

Briefly stated, the present invention is directed to a method of optically measuring ultrasound travelling in or at the surface of an object which includes steps of directing a laser beam having a predetermined frequency f to the object to produce a scattered laser beam having modulation representative of the motion of the object and receiving the scattered laser beam with two substantially identical optical interferometric systems to produce two interferometric signals. One of the two interferometric systems has a resonance frequency higher than the frequency f of the laser beam and the other has a resonance frequency lower than f. The method further includes a step of combining the two interferometric signals to generate an output representative of the motion of the object.

The present invention is also directed to an apparatus for optically measuring ultrasound travelling in or at the surface of an object which includes a laser beam source directing a laser beam having a predetermined frequency f to the object to produce a scattered laser beam having modulation representative of the motion of the surface and two substantially identical optical interferometric systems for receiving the scattered laser beam to produce two interferometric signals. One of the two interferometric systems has a resonance frequency higher than the frequency f of the laser beam and the other has a resonance frequency lower than f. The apparatus further includes means for combining the two interferometric signals to generate an output representative of the motion of the object.

BRIEF DESCRIPTION OF THE DRAWINGS

For more complete understanding of the present invention and for further objects and advantages thereof, references may now be made to the following description taken in conjunction with the accompanying drawings in which.

DETAILED DESCRIPTION OF PREFERRED EMBODIMENTS OF THE INVENTION

Figure 1:
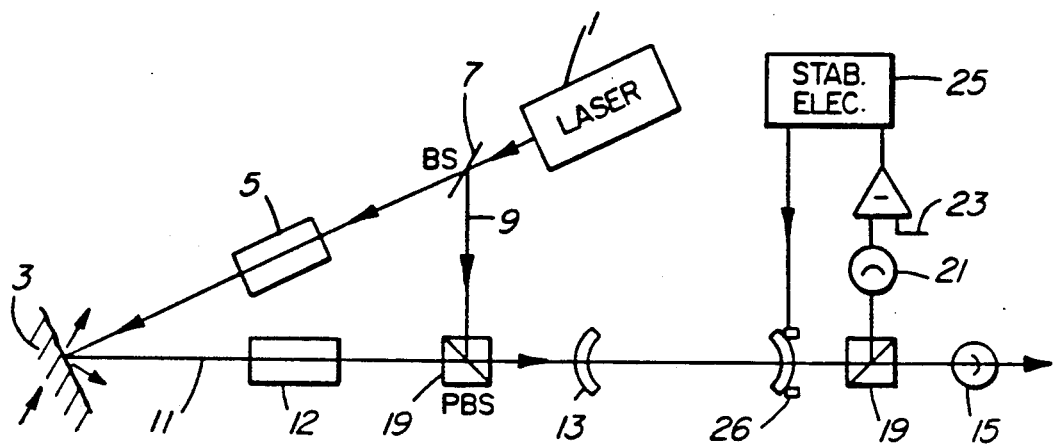
FIG. 1 is a schematic illustration of a known ultrasonic inspection system using a Fabry-Perot interferometer in the transmission mode.
Figure 2:
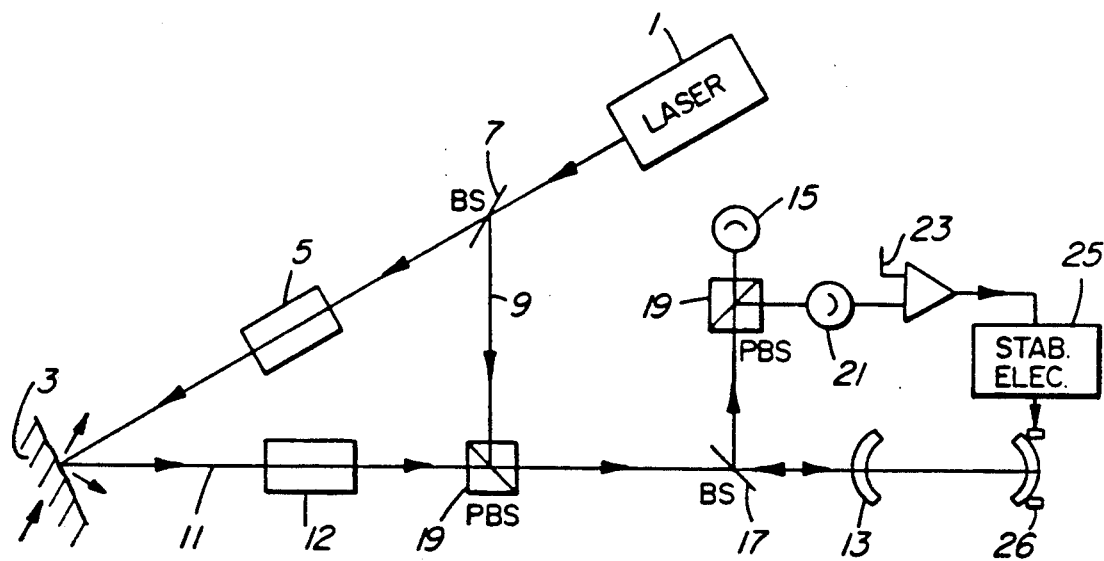
FIG. 2 is a schematic illustration of another known ultrasonic inspection system using a Fabry-Perot interferometer in the reflection mode.
Figure 3A:
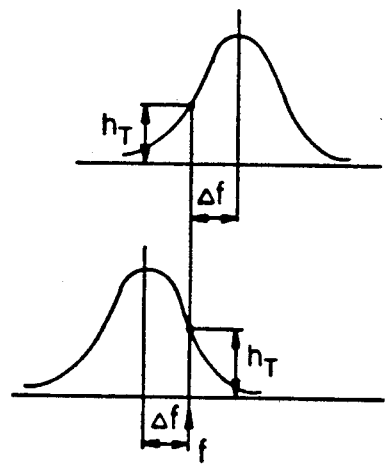
FIGS. 3a and 3b are graphs showing respectively transmission and reflection resonance curves of Fabry-Perot interferometers and stabilization points with respect to the laser beam frequency f.
Figure 3B:
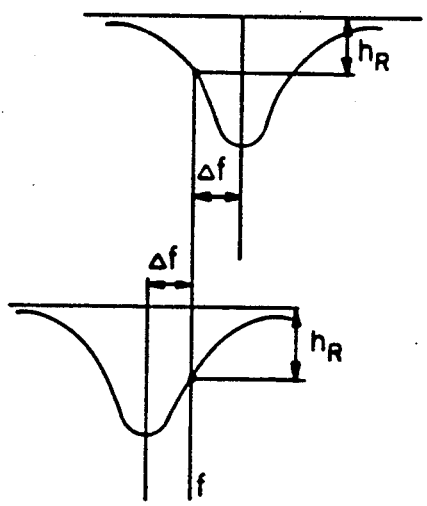

FIGS. 1 and 2 respectively illustrate schematically interferometric ultrasound detecting systems using confocal Fabry-Perot interferometer (sometimes called Fabry-Perot resonator or simply Fabry-Perot in the present specification) in the transmission mode and in the reflection mode. Like elements are designated by like numerals in the figures. A laser beam source 1 directs a laser beam having frequency f toward an object 3 through an optical arrangement 5 which may include fibers, lens, amplifiers etc.. A beam splitter 7 is provided to divide a portion 9 of the laser beam into a separate optical path to be used for stabilization and will be explained later. A scattered laser beam 11 is introduced through an optical arrangement 12 to a confocal Fabry-Perot resonator 13. In FIG. 1, the Fabry-Perot resonator has a resonance curve as shown in FIGS. 3a and 3b which respectively show transmission and reflection curves of two Fabry-Perots and their relationships with the laser beam frequency f. The Fabry-Perot resonator 13 thus transmits the scattered beam therethrough according to the curve and produces an optical signal which a signal detector 15 detects to generate an interferometric signal at its output.

In FIG. 2, the Fabry-Perot resonator is used in the reflection/sidebands stripping mode so that it reflects the scattered beam back toward a beam splitter 17 and then toward a signal detector 15. In the both figures, polarization beam splitters 19 are provided in optical paths so that differently polarized stabilization beam can be separately picked up by a stabilization detector 21 which produces stabilization voltage to be compared with a preset voltage 23. Stabilization electronics 25 adjusts the Fabry-Perot resonator by way of piezoelectric pusher 26 so that the laser frequency f is located on the slope of a transmission (or reflection) peak (generally at half maximum height).

The present invention essentially consists first of two identical confocal Fabry-Perot interferometers, the length of which have been adjusted in such a way that the laser frequency is located along one slope of the resonance peak (or dip) of one Fabry-Perot and along the opposite slope at the same height of the other Fabry-Perot. Stated in other words, the frequency detunings between the laser frequency and the cavity resonance frequencies of the two Fabry-Perot interferometers should be of opposite sign or that the laser frequency is located halfway between the interferometer resonance frequencies. The principle of this invention is explained in FIGS. 3a and 3b which show the transmission and reflection curves of two Fabry-Perot interferometers, the resonance frequencies of which have been detuned by $\Delta f$ on opposite sides of the laser frequency. The stabilization points are at the same height $h_T$ in the transmission mode or at the same depth $h_R$ in the reflection mode. The present invention further consists in sending the signals from the two detectors at the output of the Fabry-Perots (on the transmission side for the transmission/velocity interferometery mode or on the reflection side for the reflection/sidebands stripping mode) through a differential amplifier which takes the difference between them. Thus, the intensity fluctuations of the received light from the workpiece (caused by fluctuations of the laser intensity or other fluctuations along the beam path) are eliminated, whereas the phase or frequency changes associated to the surface transient motion give contributions which add up, because they are of opposite sign. These results are readily seen in FIGS. 3a and 3b when the perturbations are at low frequencies, much below the Fabry-Perot optical bandwidth. At higher frequencies, in the useful operating range of these systems, these results follow from a detailed mathematical analysis of their frequency responses to intensity changes and to phase changes and they have also been verified by experiments.

Figure 4:
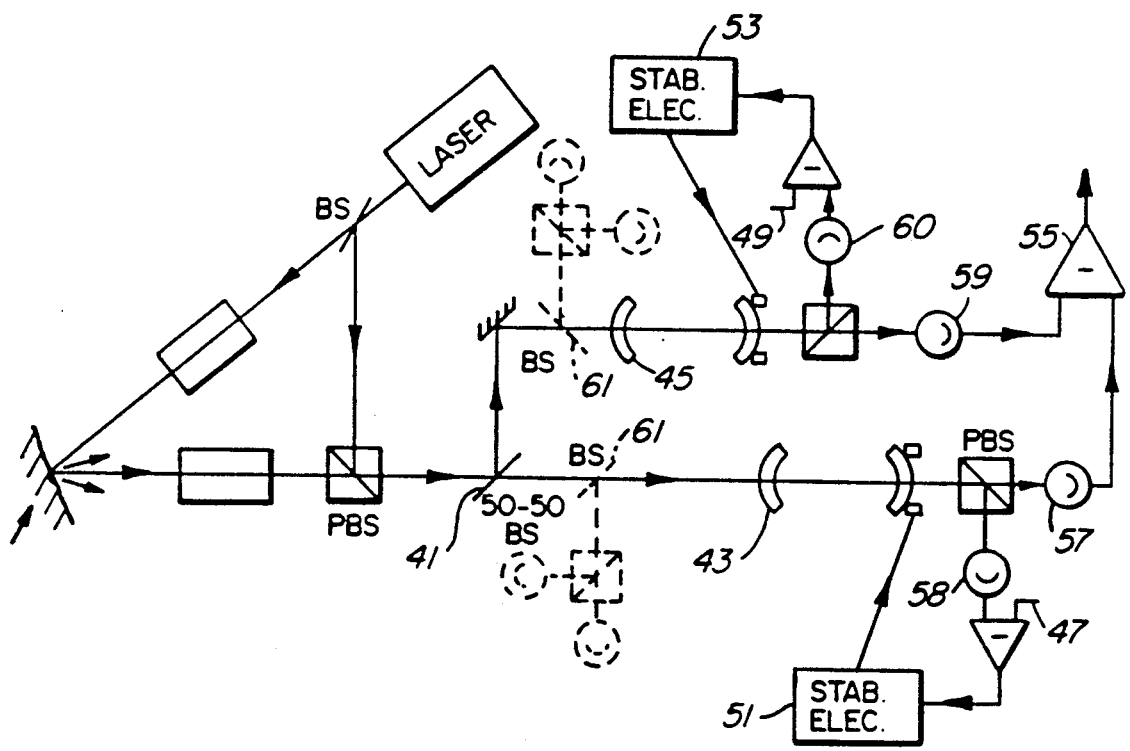
FIG. 4 is a schematic illustration of one embodiment of the present invention.

FIG. 4 shows schematically one embodiment of the invention using the velocity/transmission interferometry mode. As shown in the figure, the stabilization beam and the beam scattered by the surface are split 50% in transmission, 50% in reflection by a nonpolarizing beam splitter 41. Transmitted light is sent to the first confocal Fabry-Perot 43, where detection and stabilization are performed as in FIG. 1. Reflected light is sent to the second Fabry-Perot 45, where detection and stabilization are performed in the same way. The stabilization present levels 47 and 49 are the same because they originate from the same voltage source and stabilization networks 51 and 53 are designed to give error voltages to the piezoelectric pushers of opposite polarity (one network differs from the other by an inverting unit gain amplifier). In this way stabilization occurs at the same height on opposite slopes of the transmission peak. As seen in FIG. 4, the two signals are sent to a differential amplifier 55, according to the principle of this invention. One should also note that the two confocal Fabry-Perot interferometers 43 and 45 and two signal detectors 57 and 59 are located at equal distances from the beam splitter in order to provide identical illumination of the interferometers and to avoid any delay between the two detecting channels.

Also shown in FIG. 4, in broken lines, is the configuration applicable to the reflection/sidebands stripping mode. A 50% reflection-50% transmission nonpolarizing beam splitter 61 is located in front of each confocal Fabry-Perot interferometer and stabilization is performed as in FIG. 2. The outputs of the two signal detectors are sent to a differential amplifier according to the principle of this invention. The differential amplifier and the stabilization electronics for this embodiment are not represented in FIG. 4 for sake of clarity.

Figure 5:
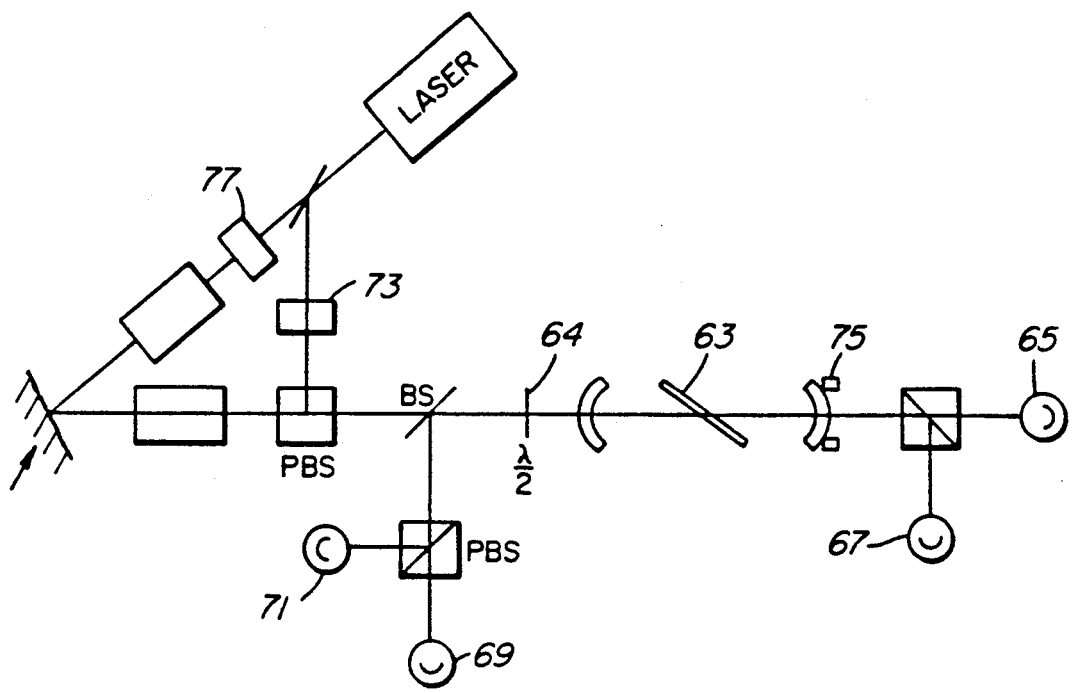
FIG. 5 is a schematic illustration of another embodiment of the present invention.

A further embodiment, which uses only a single confocal cavity, is illustrated in FIG. 5. By using two orthogonal polarizations and birefringent element inside the cavity, this cavity is made equivalent to two cavities. For one polarization, the stabilization point is on one slope of the transmission peak (or dip), whereas it is located on the opposite slope at the same height for the other polarization. Path difference between the two polarizations is provided by a birefringent plate 63 which is slightly tilted in order to find the optimum path difference. This path difference is such that the two equivalent cavities are detuned by $2\Delta f$. As seen in FIG. 5, the light from the surface and the stabilization beam, which are respectively polarized in the plane of the drawing and the plane perpendicular to it, are rotated by 45° by a half wave plate 64, so that they have equal polarization components in the plane of the drawing and in the plane perpendicular to it. In this embodiment of the velocity/transmission interferometry mode, detectors 65 and 67 are the signal detectors and are connected to the differential amplifier. The detectors 69 and 71 are used for stabilization and their outputs are compared to the same preset stabilization voltages. Since, in this case, the stabilization beam and the signal beam from the surface are not separated by polarization optics as in FIG. 4, an optical shutter 73 synchronized with the ultrasonic source is used to block the stabilization beam during detection. During this time, the stabilization level applied to the piezoelectric pusher 75 is kept at the value before ultrasonic excitation by sample-and-hold circuit. The interfering effect produced by the signal beam on the stabilization detector is eliminated by using a second optical shutter 77 in front of the laser, which is only opened during ultrasonic detection, or by using a pulse amplifier which is turned on only during detection. The same arrangement can be used for the reflection/sidebands stripping mode by having detectors 69 and 71 as signal detectors and detectors 65 and 67 as stabilization detectors.

Another stabilization scheme is also possible with such a dual confocal Fabry-Perot configuration (configuration comprising actually two Fabry-Perots or equivalent to two). In this scheme, the outputs of the two stabilization detectors are sent to a differential amplifier which provides the error signal. By referring to FIGS. 3a and 3b, it is readily verified that this difference signal changes sign when the laser frequency goes through the proper value, mid-way between the two cavity resonance frequencies. This difference signal is then sent to a stabilization network which drives both piezoelectric pushers. This assumes that the two cavities have been properly detuned (by approximately a full cavity bandwidth for best sensitivity) and maintain the same offset. This could be realized by mounting the two confocal Fabry-Perots on the same stable mechanical structure made of low expansion material such as Invar (Trade Mark) or by using the configuration with a birefringent plate shown in FIG. 5.

Figure 6:
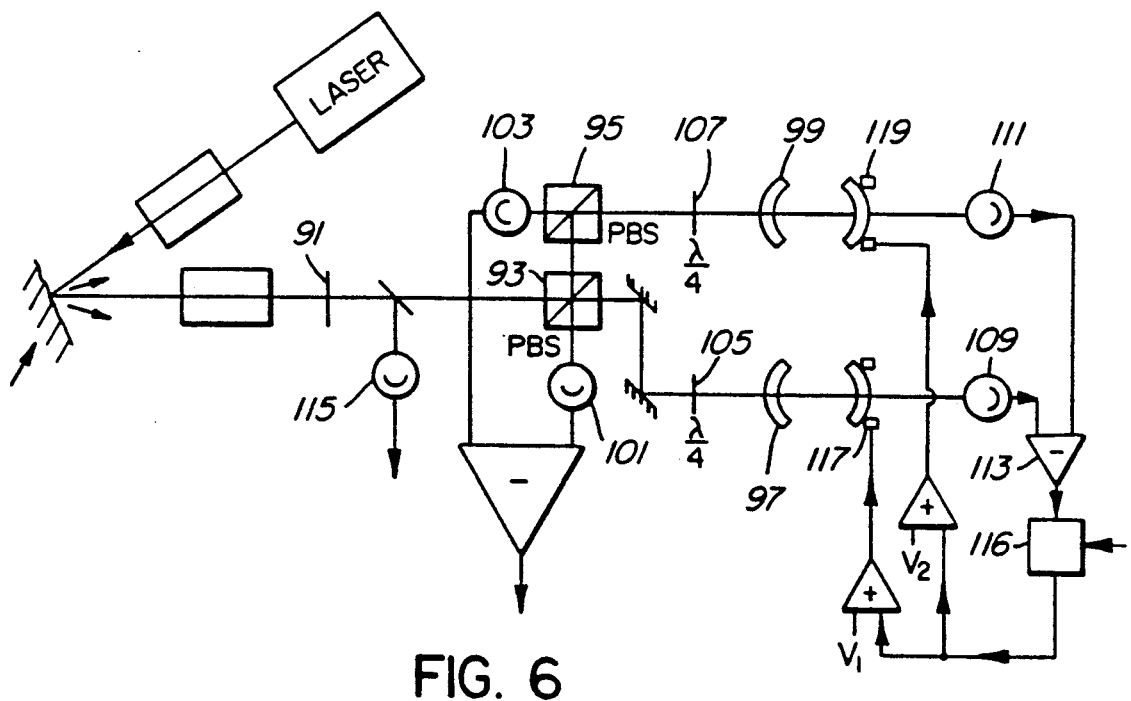
FIG. 6 is a schematic illustration of still another embodiment of the present invention.

This stabilization scheme is also applicable to the beam scattered by the surface of the workpiece and an error signal for stabilization can be derived by using only this beam without resorting to a stabilization beam directly derived from the laser. An embodiment which uses this stabilization scheme without a stabilization beam is shown in FIG. 6. This embodiment uses the reflection/sideband stripping mode.

As shown in the figure, the beam scattered by the surface of the workpiece is polarized at 45° by a polarizer 91 with respect to the polarization directions of the two polarizing beam splitters 93 and 95, thus ensuring equal illumination intensity of the two confocal Fabry-Perots 97 and 99. The location of the Fabry-Perots and of the signal detectors 101 and 103 are such to provide identical illumination and delay for the two channels. Optimum reflection is provided by the combination of a polarizing beam splitter and a quarter-wave plates 105 and 107 oriented at 45° in each channel. Stabilization is obtained by the stabilization detectors 109 and 111 located on the transmission side of the confocal Fabry-Perots. Their outputs are sent to a differential amplifier 113 which gives the error signal. Since in practice the intensity of the scattered light by the surface of the workpiece could be very variable, an additional detector 115 is located in front of the Fabry-Perots and measures the incident light intensity from the reflection of a high transmission beam splitter. The output of 115 is used to normalize the error signal by using an appropriate circuit 116, for example an analog divider. This normalized error signal after going through suitable lead-lag filters is applied to both piezoelectric pushers 117 and 119 which control the length of the confocal cavities. This signal is added to two offset voltages $V_1$ and $V_2$, each being applied to a piezoelectric pusher. The difference between these voltages determine the detuning between the cavities. Alternatively, this normalized error signal can be applied to the laser if its frequency can be controlled. The arrangement shown in FIG. 6 can also be easily converted to the velocity/transmission interferometry mode by exchanging signal and stabilization detectors. Also note that the signal detectors could also be used for stabilization by decoupling the dc and low frequency contents of the signal which is used for stabilization to its high frequency contents which is representative of the ultrasonic surface motion.

Although this invention is particularly useful for detecting ultrasound at the surface of a workpiece, it is also applicable to the detection by remote sensing of a variety of transient motions giving a frequency spectrum above the audio range. In particular, it is applicable to the detection of the high frequency contents of air turbulence occuring along the path going from the laser source to a reflecting or scattering target and the receiver. Also, if a region along the beam is seeded by particles scattering laser light and if this region is affected by turbulence, this invention could permit the detection of such turbulent motion. The principle used in this invention makes the signal quite insensitive to changes of the number of scattering particles and changes of the scattering intensity and makes it primarily sensitive to their transient motion.

Also to be noted is that the differential signal, derived from the signal detectors, is representative of all frequency or phase shifts occuring in the laser and along the beam path. The low frequency part of these shifts is used to drive the stabilization network in the case of detection of ultrasound. This low frequency part, besides originating partially from the laser, is also caused by vibrations of the workpiece or air fluctuations along the beam path. Therefore, if a stabilization beam is directly derived from the laser and is used to stabilize the confocal Fabry-Perots, a vibrometer can be realized by monitoring the differential signal. Such a vibrometer has the advantage compared to classical vibrometers based on heterodyne interferometry to have a large light gathering efficiency (etendue or throughput).

This invention is applicable with other interferrometers of the confocal Fabry-Perot type, including those which are plane-confocal (one flat mirror located at the focal distance of a concave mirror) or those equivalent to the plane-confocal configuration.

Although the present invention is particularly useful for application to interferrometeric systems of the confocal Fabry-Perot type, which have a large light gathering capability, it could be applied and be useful as well with systems which are not of the confocal type and have a reduced light gathering capability. These systems are for example planar Fabry-Perot or systems of the Fabry-Perot type built with single mode optical fibers. These fiber systems use a fiber loop and a directional coupler. At one output of the coupler resonance dips similar to the ones observed in reflection with a Fabry-Perot made of bulk mirrors are obtained when the loop length is varied. Such Fabry-Perot like fiber resonators have been described in the paper entitled "All-single-mode fiber resonator" by L. F. Stokes et al published in Optics Letters, Vol. 7, No. 6, June 1982, pp. 288-290. In addition to the description found in this paper, by inserting another coupler along the fiber loop to tap the circulating light power, resonance peaks, similar to the ones observed on the transmission side of a Fabry-Perot, can be observed as well.

We claim:

1. A method of optically measuring ultrasound travelling in or at the surface of an object, comprising steps of:
    a) directing a laser beam having a predetermined frequency f to the said object to thereby produce a scattered laser beam having modulation representative of the motion of the said object,
    b) receiving the said scattered laser beam with two substantially identical optical interferometric systems to produce two interferometric signals, one of the said two interferometric systems having a resonance frequency higher than the frequency f of the said laser beam and the other having a resonance frequency lower than the frequency f, and
    c) combining the said two interferometric signals to generate an output representative of the motion of the said object.

2. The method of optically measuring ultrasound travelling in or at the surface of an object according to claim 1, wherein:
    the said laser beam is directed onto a surface of the said object to produce the said scattered laser beam, and
    the said step of receiving comprises steps of:
        detecting the said scattered laser beam with two substantially identical interferometers of the Fabry-Perot type to produce two optical signals, one of the said two interferometers having a resonance frequency $f+\Delta f$ and the other having a resonance frequency $f-\Delta f$, where $\Delta f$ is a predetermined amount, and
        converting the said two optical signals into the said two interferometric signals.

3. The method of optically measuring ultrasound travelling in or at the surface of an object, according to claim 1, wherein:
    the said laser beam is directed onto a surface of the said object to produce the said scattered laser beam, and
    the said step of receiving comprises steps of:
        detecting the said scattered laser beam with an interferometer of the Fabry-Perot type having a birefringent element in its optical cavity so that the said interferometer has two resonance frequencies $f+\Delta f$ and $f-\Delta f$ with respect to the polarization axes of the said birefringent element, where $\Delta f$ is a predetermined amount, the said interferometer producing two optical signals, and
        converting the said two optical signals into the said two interferometric signals.

4. The method of optically measuring ultrasound travelling in or at the surface of an object, according to claim 2, further comprising steps of:
    generating two stabilization signals which are indicative of the said laser beam, and
    sending the said stabilization signals to the said two interferometers to stabilize the said resonance frequencies at preset offsets with respect to the frequency f.

5. The method of optically measuring ultrasound travelling in or at the surface of an object, according to claim 4, wherein the step of generating includes steps of:
    polarizing a portion of the said laser beam differently from the remaining part thereof,
    sending the said polarized portion through the said Fabry-Perot interferometers, and
    monitoring the said polarized portion emerging from the said Fabry-Perot interferometers to produce the said two stabilization signals.

6. The method of optically measuring ultrasound travelling in or at the surface of an object, according to claim 4, wherein the step of generating includes steps of:
    sending the said scattered laser beam through the said two interferometers, and
    monitoring the said scattered laser beam emerging from the said two interferometers to produce the said two stabilization signals.

7. The method of optically measuring ultrasound travelling in or at the surface of an object, according to claim 5, wherein:
    the said two interferometers are used in the transmission mode.

8. The method of optically measuring ultrasound travelling in or at the surface of an object, according to claim 5, wherein:
    the said two interferometers are used in the reflection mode.

9. The method of optically measuring ultrasound travelling in or at the surface of an object, according to claim 6, wherein:
    the said two interferometers are used in the transmission mode.

10. The method of optically measuring ultrasound travelling in or at the surface of an object, according to claim 6, wherein:
    the said two interferometers are used in the reflection mode.

11. An apparatus for optically measuring ultrasound travelling in or at the surface of an object, comprising:
    a) a laser beam source for directing a laser beam having a predetermined frequency f to the said object to thereby produce a scattered laser beam having modulation representative of the motion of the said object,
    b) two substantially identical optical interferometric systems for receiving the said scattered laser beam to produce two interferometric signals, one of the said two interferometric systems having a resonance frequency higher than the frequency f of the said laser beam and the other having a resonance frequency lower than the frequency f, and
c) combining means for combining the said two interferometric signals to generate an output representative of the motion of the said object.

12. The apparatus for optically measuring ultrasound travelling in or at the surface of an object, according to claim 11, wherein the said optical interferometric systems comprise:

two substantially identical interferometers of the Fabry-Perot type, one of which has a resonance frequency $f+\Delta f$ and the other of which has a resonance frequency $f-\Delta f$, where $\Delta f$ is a predetermined amount.

13. The apparatus for optically measuring ultrasound travelling in or at the surface of an object, according to claim 11, wherein the said optical interferometric systems comprise:

an interferometer of the Fabry-Perot type having a birefringent element in its optical cavity so that the said interferometer has two resonance frequencies $f+\Delta f$ and $f-\Delta f$ with respect to the polarization axes of the said birefringent element, where $\Delta f$ is a predetermined amount.

14. The apparatus for optically measuring ultrasound travelling in or at the surface of an object, according to claim 12, further comprising:

stabilization means for generating two stabilization signals which are indicative of the said laser beam, and piezoelectric means for adjusting the said two interferometers in response to the said two stabilization signals to stabilize the said resonance frequencies at preset offsets with respect to the frequency f.

15. The apparatus for optically measuring ultrasound travelling in or at the surface of an object, according to claim 14, wherein the said stabilization means comprises:

a polarization means for polarizing a portion of the said laser beam differently from the remaining part thereof, sending means for sending the said polarized portion through the said two interferometers, and stabilization detector means for monitoring the said polarized portion emerging from the said two interferometers to produce the said two stabilization signals.

16. The apparatus for optically measuring ultrasound travelling in or at the surface of an object, according to claim 14, wherein the said stabilization means comprises:

sending means for sending the said scattered laser beam through the said two interferometers, and stabilization detector means for monitoring the said scattered laser beam emerging from the said two interferometers to produce the said two stabilization signals.

17. The apparatus for optically measuring ultrasound travelling in or at the surface of an object, according to claim 13, further comprising:

stabilization means for generating a stabilization signal which is indicative of the said laser beam, and piezoelectric means for adjusting the said interferometer in response to the said stabilization signal to stabilize the said two resonance frequencies at preset offsets with respect to the frequency f.

* * * * *